United States Patent
Bright

(10) Patent No.: US 7,598,087 B2
(45) Date of Patent: Oct. 6, 2009

(54) PROTEIN IMPRINTED POLYMERS WITH INTEGRATED EMISSION SITES

(75) Inventor: Frank V. Bright, Williamsville, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 768 days.

(21) Appl. No.: 11/031,318

(22) Filed: Jan. 7, 2005

(65) Prior Publication Data
US 2005/0214876 A1 Sep. 29, 2005

Related U.S. Application Data

(60) Provisional application No. 60/534,735, filed on Jan. 7, 2004.

(51) Int. Cl.
G01N 21/64 (2006.01)
G01N 21/31 (2006.01)
G01N 33/00 (2006.01)

(52) U.S. Cl. .................. 436/164; 422/56; 422/57; 422/58; 422/82.05; 422/82.06; 422/82.07; 422/82.08; 422/82.09; 436/86; 436/87; 436/88; 436/94; 436/165; 436/171; 436/172

(58) Field of Classification Search ........... 422/56–58, 422/82.05, 82.09; 436/86–88, 94, 164–165, 436/171–172
See application file for complete search history.

(56) References Cited

U.S. PATENT DOCUMENTS 3,966,744 A    6/1976   Goldstein et al.
5,162,218 A *  11/1992  Schultz ................. 435/188
5,512,492 A *  4/1996   Herron et al. ........... 436/518
5,714,386 A    2/1998   Roederer
6,057,377 A *  5/2000   Sasaki et al. ............ 521/99
6,131,580 A    10/2000  Ratner et al.
6,221,604 B1   4/2001   Upadhya et al.
6,287,765 B1 * 9/2001   Cubicciotti ............... 435/6
6,458,599 B1 * 10/2002  Huang ................... 436/518
6,495,352 B1 * 12/2002  Brinker et al. ........... 435/176
6,525,154 B1   2/2003   Shea et al.
6,582,971 B1   6/2003   Singh et al.
6,743,581 B1 * 6/2004   Vo-Dinh .................. 435/6
6,935,165 B2 * 8/2005   Bashir et al. ........... 73/64.53
7,205,162 B1 * 4/2007   Mosbach et al. ......... 436/535
7,319,038 B2 * 1/2008   Southard ................ 436/111

(Continued)

FOREIGN PATENT DOCUMENTS

WO     WO 01/30856 A1    5/2001

OTHER PUBLICATIONS

Lulka, M. F. et al, Analytical Letters 1997, 30, 2301-2313.*

(Continued)

Primary Examiner—Arlen Soderquist
(74) Attorney, Agent, or Firm—Hodgson Russ LLP

(57) ABSTRACT

This invention provides protein or polypeptide imprinted polymers with integrated emission sites (PIPIES) for detecting the presence of a protein or polypeptide analyte comprising templated sites which are specific for the analyte. At or near the templated sites are selectively placed reporter molecules. A method is also disclosed for the preparation of the PIPIES and the use of these for the detection of analytes.

28 Claims, 10 Drawing Sheets

U.S. PATENT DOCUMENTS

| | | | |
|---|---|---|---|
| 7,384,589 B2* | 6/2008 | Hart et al. | 264/494 |
| 2002/0144626 A1 | 10/2002 | Schut | |
| 2004/0106162 A1* | 6/2004 | Glasel et al. | 435/7.32 |
| 2004/0157804 A1 | 8/2004 | Chen et al. | |
| 2006/0019408 A1* | 1/2006 | Waggoner et al. | 436/518 |

OTHER PUBLICATIONS

Makote, R. et al, Chemistry of Materials 1998, 10, 2440-2445.*

Lulka, M. F. et al, Materials Science & Engineering, C 2000, 11, 101-105.*

Dong, H. et al, Analytical Sciences 2001, 17(Suppl.), a295-a298.*

Leung, M. K.-P. et al, Journal of Materials Chemistry 2001, 11), 2985-2991.*

Zhang, H. et al, Tetrahedron Letters 2001, 42, 4413-4416.*

Angelides, K. J., Biochimica et Biophysica Acta, Protein Structure 1981, 669, 149-156.*

Yan, M. et al, Journal of the American Chemical Society 1993, 115, 814-816.*

Bronk, K. S. et al, Analytical Chemistry 1994, 66, 3519-3520.*

Turkewitxch, et al., *Fluorescent Functional Recognition Sites through Molecular Imprinting: A Polymer-Based Fluorescent Chemosensor for Aqueous cAMP*, Analytical Chemistry, 1998, vol. 70, pp. 2025-2030.

Rathbone, et al., *Molecular recognition by fluorescent imprinted polymers*, Tetrahedron Letters, 2000, vol. 41, pp. 123-126.

Graham et al.; Development and Characterization of Molecularly Imprinted Sol-Gel Materials for the Selective Detection of DDT; Anal. Chem., Jan. 15, 2002, vol. 74, No. 2; pp. 458-467.

Pirila-Honkanen; Thermodynamic and Spectroscopic Properties of 2-Pyrrolidinones. 6 Normalized $E_T(30)$ Parameters for Binary Solvent Mixtures of 2-Pyrrolidinone at 30 and 50°C; Journal of Solution Chemistry, 1995, vol. 24, No. 7; pp. 641-649.

Albert et al.; Cross-Reactive Chemical Sensor Arrays; Chem. Rev., 100; pp. 2595-2626; 2000 American Chemical Society; published on Web Jun. 24, 2000.

Bailey et al.; Sensing Volatile Chemicals Using Conducting Polymer Arrays; Polymer Sensors and Actuators; pp. 149-181; Osada, Y., DeRossi, D.E., Eds.: Springer-Verlag, Berlin, Germany, 2000.

Stephan et al.; Electrochemical Sensor Arrays; Critical Reviews in Analytical Chemistry, 1999, vol. 29, No. 2, pp. 133-153; CRC Press LLC.

Walt; Imaging Optical Sensor Arrays; Current Opinion in Chemical Biology, 2002, vol. 6; pp. 689-695; 2002 Elsevier Science Ltd., published online Aug. 30, 2002.

Cho et al.; Multianalyte Pin-Printed Biosensor Arrays Based on Protein-Doped Xerogels; Anal. Chem. 2002, vol. 74, No. 24; pp. 6177-6184; 2002 American Chemical Society, published on Web Nov. 12, 2002.

Cho et al.; Integrated Chemical Sensor Array Platform Based on a Light Emitting Diode, Xerogel-Derived Sensor Elements, and High-Speed Pin Printing; Analytical Chimica Acta 470 (2002); pp. 101-110; 2002 Elsevier Science B.V.

Cho et al.; Pin-Printed Chemical Sensor Arrays for Simultaneous Multianalyte Quantification; Anal. Chem., 2002; vol. 74, No. 6; pp. 1462-1466; 2002 American Chemical Society, published on Web Jan. 25, 2002.

Kriz et al.; Molecular Imprinting New Possibilities for Sensor Technology; Analytical Chemistry News & Features, Jun. 1, 1997; pp. 345-349.

Wulff; Molecular Imprinting in Cross-Linked Materials With the Aid of Molecular Templates-A Way Towards Artificial Antibodies; Angew. Chem. Int. Ed. Engl, 1995, vol. 34; pp. 1812-1832.

Mayes et al.; Molecularly Imprinted Polymers: Useful Materials for Analytical Chemistry?; Trends in Analytical Chemistry, 1997, vol. 16, No. 6; pp. 321-332.

Jenkins et al.; Polymer-Based Lanthanide Luminescent Sensor for Detection of the Hydrolysis Product of the Nerve Agent Soman in Water; Anal. Chem., 1999, vol. 71, No. 2; pp. 373-378; 1999 American Chemical Society, published on Web Dec. 10, 1998.

Matsui et al.; Molecularly Imprinted Polymer as 9-Ethyladenine Receptor Having a Porphyrin-Based Recognition Center; J. Am. Chem. Soc., 2000, vol. 122; pp. 5218-5219; 2000 American Chemical Society, published on Web May 12, 2000.

Liao et al.; Building Fluorescent Sensors by Template Polymerization: The Preparation of a Fluorescent Sensor for L-Tryptophan; Bioorganic Chemistry, 1999, vol. 27; pp. 463-476; 1999 Academic Press.

Avnir et al.; Encapsulation of Organic Molecules and Enzymes in Sol-Gel Glasses A Review of Novel Photoactive, Optical, Sensing, and Bioactive Materials; pp. 384-404; 1992 American Chemical Society.

Avnir et al.; Organically Doped Sol-Gel Porous Glasses: Chemical Sensors, Enzymatic Sensors, Electrooptical Materials, Luminescent Materials and Photochromic Materials; Sol-Gel Optics—Processing and Applications, Chapter 23; pp. 539-582; Klein, L.C., Ed., Kluwer: Boston, 1994.

Dave et al.; Sol-Gel Encapsulation Methods for Biosensors; Analytical Chemistry, 1994, vol. 66, No. 22; pp. 1120-1127; 1994 American Chemical Society.

Cushman et al.; Synthesis and Anti-HIV Activities of Low Molecular Weight Aurintricarboxylic Acid Fragments and Related Compounds; J. Med. Chem., 1991, Vol. 34; pp. 337-342; 1991 American Chemical Society.

Whitcombe et al.; A New Method for the Introduction of Recognition Site Functionality into Polymers Prepared by Molecular Imprinting: Synthesis and Characterization of Polymeric Receptors for Cholesterol; J. Am. Chem. Soc., 1995, vol. 117; pp. 7105-7111; 1995 American Chemical Society.

Sellergren; Noncovalent Molecular Imprinting: Antibody-Like Molecular Recognition in Polymeric Network Materials; Trends in Analytical Chemistr, 1997, vol. 16, No. 6; pp. 310-320; 1997 Elsevier Science B.V.

Whitcombe et al.; Covalent Imprinting Using Sacrificial Spacers; Tech. Instrumn. Anal. Chem., 2001, vol. 23; pp. 203-212.

Kriz et al.; Introducing Biomimetic Sensors Based on Molecularly Imprinted Polymers as Recognition Elements; Analytical Chemistry, Jul. 1, 1995, vol. 67, No. 13; pp. 2142-2144.

Sreenivasan et al.; Imparting Recognition Sites in Poly(HEMA) for Two Compounds Through Molecular Imprinting; Journal of Applied Polymer Science, 1999, vol. 71; pp. 1823-1826.

* cited by examiner

Figure 9

PROTEIN IMPRINTED POLYMERS WITH INTEGRATED EMISSION SITES

This application claims priority to U.S. Provisional Application No. 60/534,735 filed on Jan. 7, 2004, the disclosure of which is incorporated herein by reference.

This work was funded by Grant Nos. CHE-0078101 and CHE-0315129 from the National Science Foundation. The Government has certain rights in the invention.

FIELD OF THE INVENTION

This invention relates generally to the field of detection of analytes and more particularly to the detection of proteins in a sample.

BACKGROUND OF THE INVENTION

Americans spend billions of dollars annually on the detection and quantification of chemical substances. Most of these measurements are performed in well-outfitted laboratories, requiring skilled personnel, large amounts of costly reagents, and long analysis times. Also, the demands for use in clinical point-of-care testing or for field deployment necessitate small, integrated analytical platforms. Many of these needs have helped to spark chemical sensor development [1]. Similarly, the ever growing need to simultaneously measure "everything" in a sample [2] has pushed the development of artificial "noses" and "tongues" [3] which depend upon chemical and biochemical sensor array strategies [4-10].

Presently, there is a need to develop new devices which overcome the disadvantages of presently used devices and methods. Detection methods which allow the simultaneous quantification of multiple analytes in a sample, are less expensive and more simple to construct and operate, are accurate, precise and reliable, and/or provide adequate detection limits and selectivity would be a welcome advance in the field of analyte detection.

One general device which has been tried for detection is the "biosensor." In the generic biosensor, an immobilized biorecognition element (e.g., an antibody, aptamer, DNA oligonucleotide, enzyme, lectin, signaling protein, transport protein) serves to selectively recognize a target analyte and the binding or conversion (if the analyte is a substrate) event leads to an optical, mass, thermal, and/or electrochemical response that is related to the analyte concentration within the sample.

Although biosensor development may appear simple, there are many fundamental issues associated with developing analytically useful biosensors. For example, traditional strategies depend upon identifying an appropriate biorecognition element that can selectively recognize the target analyte. A suitable detection/transduction method is used and the biorecognition element is immobilized [11-13] such that it retains its native activity/affinity and selectivity. The biorecognition element—the biosensor's heart in a traditional design—needs to remain stable over time, the target analyte needs to have access to the biorecognition element, and the analyte-biorecognition element association/interaction needs to be reversible or at least easily dissociated/reset following each measurement. The foregoing shortcomings have limited the application of biosensors in analyte detection.

Over the past decade, the introduction of specific binding domains within synthetic polymers by template-directed cross-linking of functional monomers has attracted considerable attention [14,15]. Molecular imprinting involves arranging polymerizable functional monomers around a template (pseudo-target analyte or the actual target analyte) followed by polymerization and template removal. The arrangement is typically achieved by: (i) non-covalent interactions (e.g., H-bonds, ion pair interactions) or (ii) reversible covalent interactions. After template removal, these molecularly imprinted polymers (MIPs) can recognize and bind specific chemical species (i.e., the template or template analogs).

Potential advantages of MIP-based materials include: specificity comparable to a biorecognition element; robustness and stability under extreme chemical and physical conditions; and an ability to design recognition sites for analytes that lack suitable biorecognition elements. MIPs have been developed for (not an exhaustive list) proteins, amino acid derivatives, sugars and their derivatives, vitamins, nucleotide bases, pesticides, pharmaceuticals, and polycyclic aromatic hydrocarbons. However, according to Lam [16], one of the major issues in the development of MIP based biomimetic sensors is signal transduction.

There are several reports of MIP-based sensors that exploit luminescence as the transduction modality. For example, the Powell group [17a] formed cAMP-imprinted organic polymers by using trans-4-[p-(N,N-dimethylamino)stryl]-N-vinylbenzylpyrimidinium chloride (fluorophore), trimethylolpropane trimethacrylate, 2-hydroxyethyl methacrylate, and the initiator, 2,2'-azobisisobutyronitrile (AIBN). These MIPs showed a 20% change in fluorescence in the presence of 1 millimolar cAMP and they were selective for cAMP over cGMP. The Murray group [17b] prepared Soman-imprinted organic polymers by using $Eu(R)_3(NO_3)_3$ (R=pinacolyl methylphosphonate or divinylmethyl benzoate) (fluorophore), styrene, and AIBN. These MIPs were able to detect Soman down to 750 parts per quadrillion and interferences from organophosphorous pesticides was minimal. The sensor response time was 8 min. The Takeuchi group [17c] reported a fluorescence-based MIP sensor for the detection of 9-ethyladenine (9-EA). This sensor was based on templating 9-EA with 5,10,15-tris(4-isopropylphenyl)-20-(4-metharcyloyloxyphenyl)porphryin zinc (II) (fluorophore) and methacrylic acid. In $CH_2Cl_2$, these polymers exhibited a 9-EA binding affinity of $7.5 \times 10^5$ $M^{-1}$, were selective over adenine, 4-aminopyridine, and 2-aminopyridine, and yielded a fluorescence change of 40% in the presence of 250 micromolar 9-EA. The Wang group [17d] reported on a fluorescence-based MIP sensor for detecting L-tryptophan that used a dansylated dimethylacrylic acid monomer (fluorophore), ethyleneglycol dimethylacrylate, and AIBN. In operation the authors loaded a mobile quencher, 4-nitrobenzaldehyde (4-NB), into the MIP which quenched the dansyl emission. Upon addition of L-tryptophan some of the 4-NB was liberated/blocked from accessing the dansyl residue and the dansyl fluorescence increased. The change in fluorescence upon adding 10 millimolar L-tryptophan was 45%. The presence of an equivalent amount of D-tryptophan, L-phenylalanine, and L-alanine caused 32%, 27%, and <9% changes in fluorescence. The Lam group [16] used a photoinduced electron transfer (PET) strategy to form a fluorescence-based MIP for the detection of 2,4-dichlorophenoxyacetic acid (2,4-D) within a templated sol-gel-derived xerogel. In this work, the authors copolymerized 3-[N,N-bis(9-anthrylmethyl)amino)] propyltriethoxysilane (fluorophore) with tetraethoxysilane (TEOS) and phenyltrimethoxysilane (PtrMES) using 2,4-D as the template. The so formed MIP exhibited a change in fluorescence with pH (apparent pKa near 7.2) and it yielded a 15% decrease in fluorescence in the presence of 750 micromolar 2,4-D. Tests with benzoic acid and acetic acid at similar concentrations did not cause significant interference.

More recently, Edmiston and coworkers [17e] reported an approach to fabricate a fluorescence-based xerogel MIP for the detection of the pesticide 1,1-bis(4-chlorophenyl)2,2,2-trichloroethane (DDT) by using a sacrificial spacer (SS) scheme [18] wherein they reacted 3-isocyanatopropyltriethoxysilane with 4,4'-ethylidenebisphenol to form the SS. They then prepared the fluorescent monomer by reacting 3-aminoproplytriethoxysilane (APTES) with the fluorophore 4-chloro-7-nitrobenzofurazan (NBD) (attaching the NBD to the APTES amine, NBD-APTES). The imprinted xerogel was then formed by mixing NBD-APTES, SS, and bis(trimethoxysilyl)benzene followed by a typical acid hydrolysis protocol. Once the xerogel was formed, the authors cleaved the SS carbamate bond with dilute $LiAlH_4$ to form amine residues within the template site, and liberating the SS from the xerogel. The sensor responded to DDT (3% change in NBD fluorescence) and the templated xerogels offered selectivity for DDT over potential interferents (e.g., anthracene (A), 2,2-bis(4-chlorophenyl)-1,1-dichloroethylene (p,p-DDE), 1-(2-chlorophenyl)-1-(4-chlorophenyl)-2,2-dichloroethane(o,p-DDD), 2,2-bis(4-chlorophenyl)-1,1-dichloroethane (p,p-DDD),diphenylnethane (DPM), 4,4'-dibromobiphenyl (DBBP), 4,4'-bis(chloromethyl)-1,1'-biphenyl (BCP)). The DDT detection limits were at the single digit part per billion level.

However, in all previous work on luminescence based MIP sensors, no strategy has been developed to ensure that the luminescent reporter molecule is actually in immediate proximity to the analyte when the analyte binding occurs.

SUMMARY OF THE INVENTION

The present invention provides molecularly imprinted polymers and methods of using same for the selective detection of proteins and polypeptides. The method of making the molecularly imprinted polymers comprises making a protein or polypeptide templated polymer with integrated emission sites (PIPES) meaning a reporter molecule is selectively implanted at or near the templated site. For detecting the presence of the protein or polypeptide in a test sample, the test sample is exposed to the PIPES to allow the target protein or polypeptide, if present, to associate/react with the PIPIES. The sensor response can be detected by using any photonic detection device such as a photomultiplier tube, charge transfer device (CTD), or complementary metal oxide semiconductor (CMOS).

The PIPIES of the present invention are produced by first forming a polymer platform around a target protein. The protein molecule is then removed from the polymer platform, creating the templated site. The templated site is then selectively labeled with one or more reporter molecules as follows. A reporter molecule is covalently attached to an activable chemical residue to form an activable reporter. The reporter molecule may be attached to the activable chemical residue either directly or through an intervening chemical moiety tether and/or linker group. The combination of reporter molecule and activable chemical residue, with or without the tether and/or linker group, is termed as activable reporter (AR).

The activable reporter or activable reporters is/are then allowed to bind to the target protein (or polypeptide) molecule to form a non-covalently bonded target protein-AR complex. These complexes may have more than 1 reporter molecule. Reporter molecules are generally known in the art to bind to proteins and polypeptides via non-covalent binding including hydrophobic and hydrogen bonding. The target protein molecule acts as a delivering protein to deliver the reporter molecule(s) to the templated sites. The templated sites within the polymer matrix are then exposed to the target protein-AR complex. Upon activation of the AR, such as by a photon in the case of a photoreactivable chemical residue, a chemical reaction takes place between the activable residue on AR and the template site within the polymer matrix to form one or more covalent bonds between the activable residue on AR and the template site. This installs one or more reporter molecules at or near the template site.

While not intending to be bound by any particular theory, it is thought that changes in the physicochemical properties (e.g., dielectric constant, refractive index, dynamics, etc.) of the immediate microenvironment (referred to herein as a reporter's cybotactic region) that surrounds the reporter molecules cause changes in the reporter molecule's absorbance, excitation and emission spectra, excited-state luminescence lifetime and/or luminescence polarization. As a result, a greater change in reporter absorbance/luminescence properties (i.e., analytical signal) is expected to be realized when the reporter molecules and the template site share some or all of the reporter molecule's cybotactic region. Hence, when analyte molecules are bound to a template site thereby changing the physicochemical properties of the template site, the binding is sensed simultaneously by the reporter molecule at the template site.

Following attachment of the AR to the templated site, the delivering protein (or polypeptide) is removed by a washing step. Although it is most convenient to use an aqueous solution, other solvents like organic solvents or mixtures can also be used. The polymeric platform with the reporter(s) installed at or near the templated site is referred to herein as PIPIES. When the polymer is a xerogel, the material of the present invention is the protein imprinted xerogel with integrated emission sites or PIXIES.

Although the word protein is used throughout the application to describe the invention, this is intended to also include polypeptides. The PIPIES can be used for detecting the presence of the target protein in a sample by exposing the PIPIES to the sample. If the target protein is present in the sample, it selectively binds to the templated site. The binding of the target protein (i.e., analyte) to the templated site produces changes in the cybotactic region that surrounds the reporter molecule(s). Such changes in reporter molecule's local microenvironment can cause changes in the absorbance, excitation and emission spectra, excited-state lifetimes and/or polarization of the reporter molecule(s), and the presence of the bound protein is determined by measuring such changes.

The present invention provides a means for selectively installing reporter molecules in proximity of protein binding sites without occluding the sites. Thus, in the polymer matrix, the majority (>50%) of the reporter molecules are present at or near the templates sites. In one embodiment, substantially all the reporter molecules are present at or near the template sites. By the term "substantially all" is meant that at least about 90% of the reporters, preferably at least about 95%, more preferably at least about 98% or 99% of the reporters are present at or near the template site. In other words, in this embodiment, less than 10%, preferably less than 5%, more preferably less than 2% or 1% reporters are present in the polymer matrix and not associated with the templated sites. Therefore, unlike other methods, the bulk of the polymer platform (i.e., non-templated regions of the polymer) of the present invention is essentially free of reporters. Thus, background signal from reporters which are randomly distributed in the polymer platform and remote relative to the template sites is minimized or eliminated.

Thus, the present invention overcomes two challenges to develop MIP-based sensors for the detection of proteins. First, a protein selective polymer based MIP is formed. Second, a reporter molecule is installed at or near the template site to transduce the subsequent protein template site binding event. We term our new sensor materials as protein imprinted polymers with integrated emission sites (PIPIES). The method of the present invention is illustrated in FIGS. 1-3.

BRIEF DESCRIPTION OF THE DRAWINGS

FIG. 9 is a representation of the selectivity provided from a standard enzyme linked immunoadsorption assay (ELISA) in comparison to four (4) diversified PIXIES-based sensor arrays with 10, 100, 512, and 1024 elements each sensor element derived from a different xerogel precursor formulation.

DETAILED DESCRIPTION OF THE INVENTION

Figure 1:
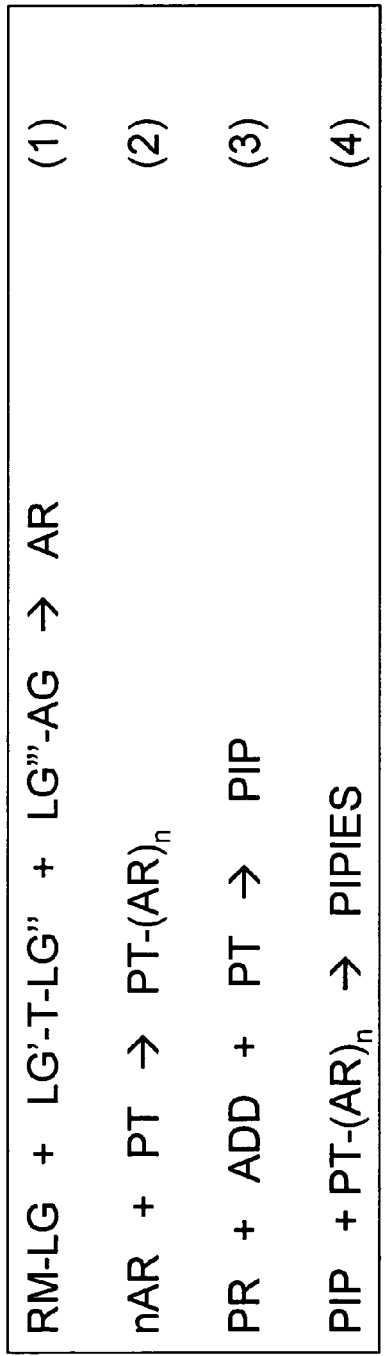
FIG. 1 is a representation of the entire process to create a PIPIES.

The present invention provides methods and compositions for molecularly imprinting a polymer for a given target protein and then site-selectively installing one or more reporter molecules at or near the template site for protein detection (FIG. 1). A method is also provided for detection and quantification of proteins by using the PIPIES-based-sensors. While reference is generally made to the detection of proteins for illustrative purposes, it is intended to encompass both proteins and polypeptides. Generally, polypeptides are considered to be made up of about 50 to 500 amino acids and proteins of more than 500 amino acids. By using the method of the present invention, sensors can be developed for unknown polypeptides or proteins even if there is no available biological recognition element.

The MIP can be formed by using any strategy known in the field of molecular imprinting based on organic and/or inorganic precursors. Many different types of polymer systems can be used in the method of the present invention. As an illustrative example, a sol-gel derived xerogel can be used. However, the approach can easily be adapted to other MIPs based on aerogels or natural or synthetic polymer systems. However, sol-gel-derived xerogels and aerogels are particularly useful because the physicochemical properties of these materials can be tuned by one's choice of precursor(s), the molar ratio of the precursors, and the processing protocol [see references 18 and 19].

In general, the polymer used in the method of this invention should be such that the target protein-activable reporter complex can bind to or otherwise interact chemically to at least some of its component monomers prior to polymerization. Such polymers are well known in the art. Examples of suitable polymerization precursors include, but are not limited to $(EtO)_3$—Si—R'—Si—$(EtO)_3$ and $(EtO)_3$—Si—R" groups as shown in FIG. 3.

According to the method of the present invention, a target protein is mixed with one or more polymerizable precursors (e.g., organic monomers, initiators, tetraalkoxysilanes, organically modified silanes, catalysts (such as an acid or a base)). Optionally, additives (e.g., organic, inorganic polymers, biopolymers, surfactants) can be used to reduce or prevent the denaturation of proteins. The polymerization is allowed to proceed so as to sequester the protein within the matrix, imprinting the matrix. The protein-doped mixture is then allowed to form a monolith (which is typically considered to be greater than 1 mm thick) or it is deposited onto a substrate as a film (which is typically considered to be equal to or less than 1 mm thick). The protein is then removed from the templated matrix (by using an aqueous buffer wash). Next, reporter molecules are covalently attached within the templated sites. This step is accomplished by the use of an activatable reporter. An activatable reporter comprises (a) a reporter, (b) an activatable chemical residue, and optionally (c) a tether/linker between the reporter and the activable chemical residue.

Figure 3:
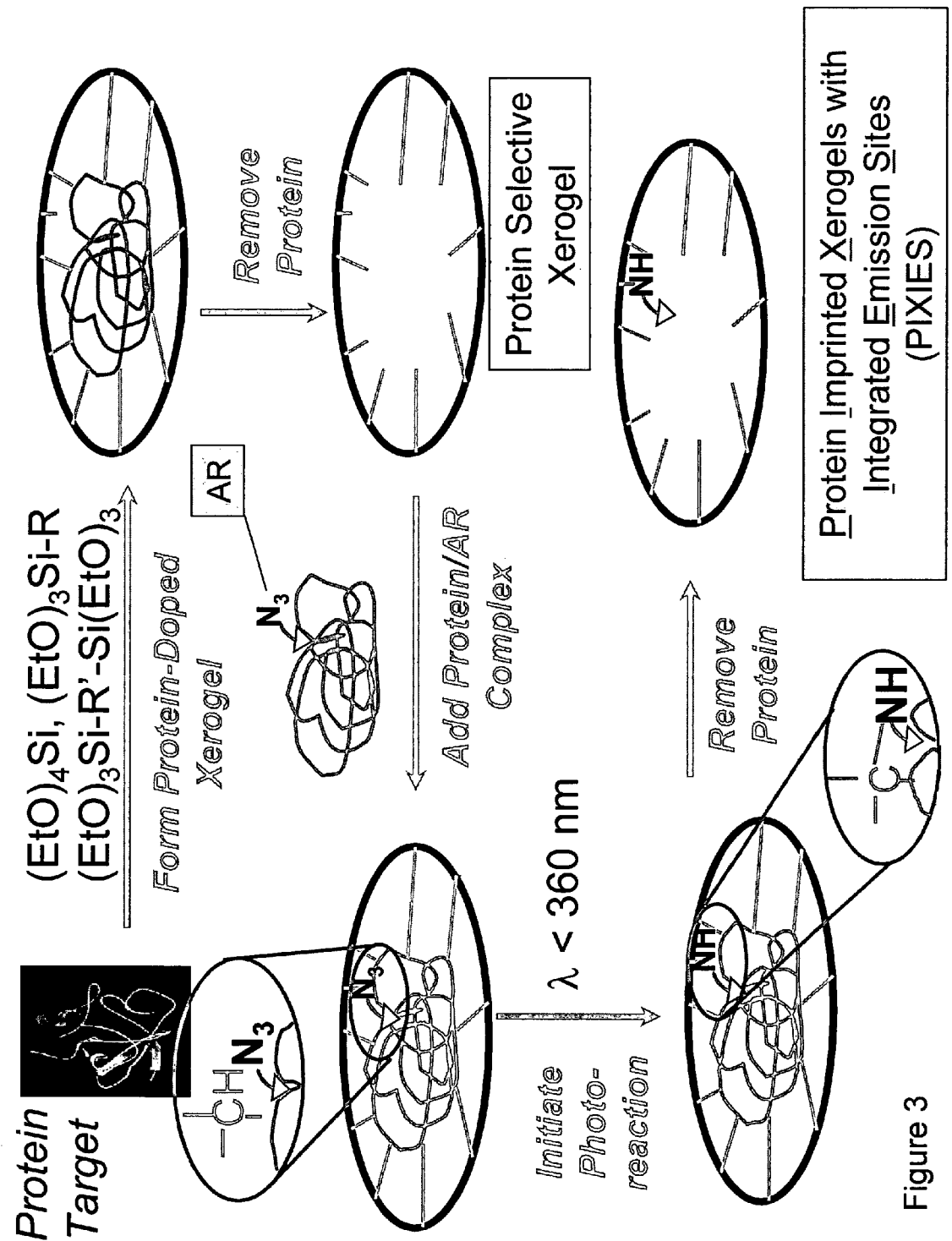
FIG. 3 is a representation of a reaction sequence for preparing a protein imprinted xerogel with integrated emission sites (PIXIES).

Useful polymer precursors include alkoxides and organically modified silanes (species with the R or R' groups in FIG. 3). These are mixed with one or more tetraalkoxysilane (tetramethyl orthosilane, TMOS or tetraethyl orthosilane, TEOS), ethanol or other suitable cosolvent, and an acid or base catalyst (e.g., HCl, NaOH). Typical R and R' groups include the following: R=n-alkyl, —$(CH_2)_3$—CHO, —$(CH_2)_3$—$NH_2$, -phenyl, -phenyl-$NH_2$, —$(CH_2)_2$-pyridyl, -cycloaminopropyl, —$CH_2$—NH-phenyl, —$(CH_2)_3$—N$(C_2H_4$—OH$)_2$ $(CH_2)_3$—$N^+$-$(R")_3$, dihydroimidazole, ureidopropyl, and EDTA; R'=—$(CH_2)_3$—NH—$(CH_2)_3$—, —$(CH_2)_3$—NH—$C_2H_4$—NH$(CH_2)_3$—, -phenyl-, and -biphenyl-]. The exact mole ratio of these precursors, the precursor form, catalysts, and additives depends on the desired xerogel one is forming.

Reporters are generally luminophores or chromophores which absorb or emit in the ultraviolet, visible or infrared. Non-limiting examples of reporters which can be used in the process of the present invention include luminescent organic or inorganic species like fluorescein, boron-dipyrromethene (BODIPY), rhodamine, organometallic complexes like tris(4,7- diphenyl -1, 10 -phenanthroline)ruthenium(II) ([Ru(dpp)$_3$]$^{2+}$ and luminescent nanoparticles (i.e., quantum dots). Non-luminescent dye molecules that are responsive to their physicochemical environments can also be used as reporter molecules (e.g., 4-nitroaniline, and 2,6-diphenyl-4-(2,4,6-triphenyl-1-pyridinio)phenolate (Reichardt's dye 30), 2,6-dichloro-4-(2,4,6-triphenyl-1-pyridinio)phenolate (Reichardt's dye 33), and N,N-diethyl-4-nitroaniline).

The combination of reporter molecule and activable residue, with or without the tether, is the activable reporter (AR). Activatable residues are chemical groups which can be activated subsequently to undergo an insertion reaction with the polymer base or other covalent bond. Groups which can be activated by absorption of a photon, such as aryl azides that generate reactive intermediates upon illumination (usually at <360 nm) that can form bonds with nucleophilic groups; fluorinated aryl azides that upon UV photolysis generate reactive nitrenes, thereby producing more C—H insertion products than the simple aryl azides or benzophenone derivatives that can be repeatedly excited with electromagnetic radiation at <360 nm until they generate covalent adducts, without loss of reactivity, can be used. Other examples of chemically reactive functional groups include: (a) for amines, isothiocyanates, succinimidyl esters, carboxylic esters, tetrafluorophenyl esters, carbonyl azides, sulfonyl chlorides, arylating agents and aldehydes; (b) for thiols, iodoacetamides, maleimides, alkyl halides, arylating agents, and disulfides; (c) for alcohols, dichlorotriazines, N-methylisatoic anhydride, aminophenylboronic acids, isocyanates prepared from acyl azides, and acyl nitriles; and (d) for carboxylic acids, hydrazines, hydroxylamines amines, carbodiimides, esterification reagents, diazoalkanes, alkyl halides, and trifluoromethanesulfonates. These groups can also function as linker groups.

The connecting moiety (also referred to herein as a tether or chemical tether) can be one of any possible natural or synthetic groups that have been used to space residues apart from one another in the chemical sciences. General examples of connecting moieties are methylene chains, ether chains, polydimethylsiloxane chains, polystyrene chains, amino acid chains, and any other organic/inorganic oligomer. Specific examples of chemical groups that can be used to form linkages between specific types of reporter molecules and activable residues include, but are not limited to the following: to link an amine residue one can use isothiocyanates, succinimidyl esters, carboxylic esters, tetrafluorophenyl esters, carbonyl azides, sulfonyl chlorides, arylating agents and aldehydes; to link a thiol residue one can use iodoacetamides, maleimides, alkyl halides, arylating agents, and disulfides; to link an alcohol residue one can use dichlorotriazines, N-methylisatoic anhydride, aminophenylboronic acids, isocyanates prepared from acyl azides, and acyl nitriles; and to link a carboxylic acid one can use hydrazines, hydroxylamines amines, carbodiimides, esterification reagents, diazoalkanes, alkyl halides, and trifluoromethanesulfonates.

To site-selectively install the reporter at or near the protein templated site, the protein is mixed with an AR (FIG. 1). The protein and the activable reporter form a complex in solution—termed herein as the protein-AR complex.

The protein-templated polymer materials are exposed to the protein-AR reporter complexes, filling accessible templated protein sites with the complexes. In this step, the target protein selectively delivers an AR molecule or AR molecules such that the templated site is within the reporter molecule's cybotactic region. The protein-AR loaded MIPs are then activated by an appropriate means (e.g., illumination with UV light). As a result, one or more reporter molecules become covalently attached at or near the templated site. In the case of a photoactivated residue which creates an attachment to the polymer platform via an insertion reaction, the templated polymer is illuminated with the appropriate wavelength of electromagnetic radiation to create, for example, a nitrene which undergoes high efficiency C—H insertion into the template site. Other insertion/bond formation reactions are within the purview of those skilled in the art of synthetic chemistry. Non-limiting examples include aryl azides that generate reactive intermediates upon illumination, fluorinated aryl azides that upon UV photolysis generate reactive nitrenes, benzophenone derivatives that can be continuously excited/illuminated with electromagnetic radiation until they generate covalent adducts, maleimides with sulfhydryls, carbodiimide with amines/carboxylates, NHS-esters with amines, hydrazides with carbohydrate (oxidized), PFP-esters with amines, hydroxymethyl phosphines with amines, psoralens with thymine (photoreactive intercalator), imidoesters with amines, pyridyl sisulfide with sulfhydryls, isocyanates with hydroxyls (non-aqueous), and vinyl sulfones with sulfhydryls, amines, or hydroxyls.

The protein-templated materials are then rinsed with a solution (such as aqueous buffer) to liberate any protein and unreacted reporter. Washing also removes any protein to which the AR may have reacted. The polymer platform that is left is a protein imprinted polymeric material with an integrated emission site.

This strategy is applicable to any MIP-based protein detection strategy. The PIXIES strategy is described in detail herein but the application to other imprinted materials will be known to those skilled in the field.

In another embodiment, the present invention provides a molecularly imprinted polymer for detecting the presence of a protein or peptide analyte comprising at least one templated site bearing exposed reactive groups in an arrangement such that the site is capable of selectively binding said protein or polypeptide analyte, wherein a reporter molecule is attached at or near the templated site. By at or near the templated site is meant that the templated site is within the cybotactic region of the reporter so that changes in the reporter molecule's absorbance, excitation and emission spectra, excited-state luminescence lifetime and/or luminescence polarization are effected when protein binds to the template site.

By selectively placing the reporter molecules at or near the templated sites, the background noise is reduced compared to that observed when the reporter molecules are only randomly distributed throughout the polymer matrix. In the present invention, while reporter molecules may be randomly distributed, an improvement in the signal to background ratio will be seen if there is also site-selective placement of the reporter molecules at the templated sites. In one embodiment, the majority (>50%) of the reporter molecules are present at or near the templated sites. In progressively preferred embodiment, at least 60%, 70%, 80%, 90%, 95%, 98% and 99% of the reporter molecules are present at or near the templated sites.

In a further embodiment, the present invention provides a method for detecting a protein. The method comprises providing a protein-templated polymer, according to the embodiment above, which can selectively bind to a protein. If the absorption/emission of the protein-templated polymer is not known, it can be measured. This PIXIES is then exposed to a test or unknown sample. The absorption/emission of the templated polymer is again measured. A change in the absorption/emission of the protein-templated polymer corresponds to the level of the protein in the sample. An appropriate calibration curve is used to determine the protein concentration in the sample.

The PIPIES of the present invention can be reused. The binding of the analyte (from a test sample, for example) is reversible and the analyte can be removed by washing with a solvent (aqueous or organic or mixtures). The PIPIES can then be used again for the detection of analytes.

In one embodiment of the invention, multiple tunable sensors can be designed and developed for each target protein. This strategy avoids the basic problems associated with single analyte/single sensor schema. Here, simultaneous screening of PIXIES libraries (cf., Table 1) can be performed to optimize PIXIES analytical performance and identify sets of PIXIES wherein the response characteristics, within the set, exhibit the greatest diversity for a given analyte.

In yet another embodiment, multiple PIXIES-based sensor elements can be formed on the face of an LED, other suitable light source, or substrate to form sensor arrays. Formation of sensors on the face of an LED and detection of analytes is described in U.S. Pat. Nos. 6,492,182, 6,582,966 and 6,589,438 incorporated herein by reference. Each sensor element can serve as an individual PIXIES-based sensor for a particular target protein.

Additionally, one can construct arrays of diversified, multimodal sensor elements wherein multiple sensors are developed for each target protein. In operation, the LED serves as the light source to simultaneously excite the reporter molecules within the sensor elements on the LED face and the target analyte-dependent emission from all the sensor elements can be detected by an array detector (e.g., CTD or CMOS). The emission from each PIXIES element is then related, after appropriate calibration steps, to the analyte concentration for the particular analyte in the sample.

For detection of absorbance/emission from a single PIXIES sensor element one can use a PMT, photodiode or other suitable photonic detector. For multiple PIXIES sensor elements one can use an imaging device such as charge coupled devices (CCDs) or CMOS based image detector. With an array detector one can simultaneously evaluate multiple PIXIES-based sensor elements.

In another embodiment, pin printing methodolgies or other array fabrication schema can be used to develop sensor arrays for simultaneous muti-analyte detection. This allows imprinting of a plurality of photonic sensor elements on the face of a light source or suitable substrate.

The following description will provide specific examples of the present invention. Those skilled in the art will recognize that routine modifications to these embodiments can be made which are intended to be within the scope of the invention.

EXAMPLE 1

This example (FIG. 1) describes the preparation of a generic PIPIES. Reaction 1 illustrates the process of forming the activable reporter (AR) molecule from a reporter molecule (RM) with a linker group (LG), an optional tether with linker groups (LG', LG"), and an activable group (AG) with a linker group (LG'''). Reaction 2 illustrates the process of forming the protein template (PT, target analyte)—AR complex (PT-(AR)$_n$. The AR to PT stoichiometry is n to 1, wherein n can be an integer. In one embodiment, n is between 1 and 10. Reaction 3 illustrates the process of forming the protein imprinted polymer (PIP) from precursors (PR), optionally additives (ADD), and protein template (PT). Reaction 4 illustrates the process of converting a PIP to a PIPIES by using the protein template (PT, target analyte)—AR complex (PT-(AR)$_n$.

EXAMPLE 2

Figure 2:
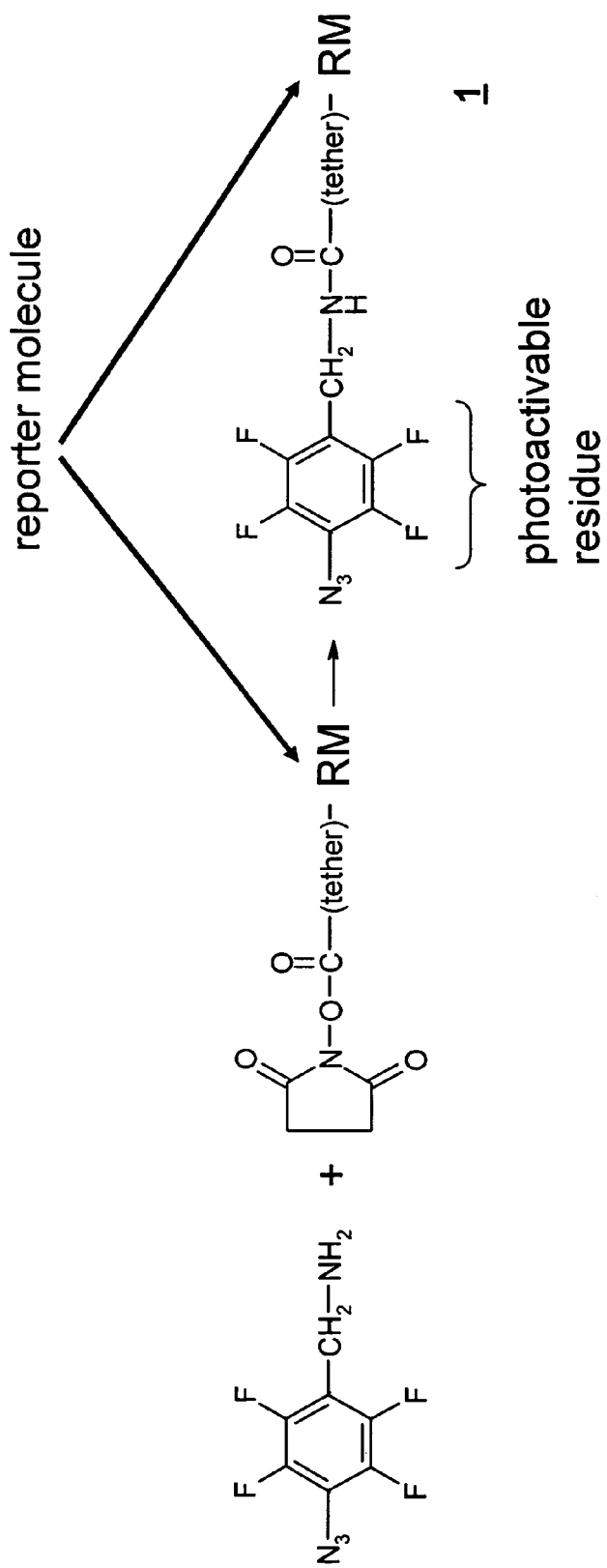
FIG. 2 is a representation of the creation of an activable reporter (AR) molecule that can be subsequently photoactivated.

This example describes the preparation of a PIXIES specific for ovalbumin. The AR was prepared as shown in FIG. 2. A reporter molecule (RM) having an activable aryl azide group connected via a tether is prepared. In the dark, an amine-reactive succinimidyl ester that is attached to a fluorinated aryl azide was reacted with an amine-containing luminophore (BODIPY 505/515) to form a luminophore-tagged aryl azide (compound 1). Compound 1 is the AR and it was used to install one or more reporter molecules within the protein templated sites within the xerogel as described below.

The protein-templated xerogel was formed (FIG. 3) by mixing 1 eq of the target protein (Ovalbumin) with 250-1000 eq of alkoxide(s). After allowing the sol to hydrolyze in a sealed vial, thin films (500-800 μm, determined by profilometry) were spun cast onto a fused silica substrate and the xerogel was allowed to form (48 h, dark, room temperature). The Ovalbumin was removed from the templated xerogel by using an aqueous buffer wash (phosphate buffered saline, pH 7.0, 0.01 M, 15 mM NaCl).

To install the luminescent reporter molecule in the Ovalbumin-template site within the xerogel, a 1:1 mixture of Ovalbumin (micromolar protein) and Compound 1 was prepared in phosphate buffered saline (pH 7.0, 0.01 M, 15 mM NaCl). Under these conditions, steady-state fluorescence anisotropy measurements showed that >98% of Compound 1 was Ovalbumin bound. The interaction between Ovalbumin and 1 is not unique; there is a large body of literature on the binding of organic and inorganic "ligands" to proteins.) Thus, the target protein (Ovalbumin) was essentially used to selectively deliver the reporter molecule(s) (RM in FIGS. 1 and 2) into the template site. We then immersed the Ovalbumin-templated xerogel films in the Ovalbumin-1 solution, filling all accessible Ovalbumin-templated sites. After 15 min, the films were removed from the Ovalbumin-1 solution. The films were illuminated with the filtered output ($\lambda$<360 nm) from a 1000 W xenon arc lamp. While not intending to be bound by any particular theory, it is considered that photoillumination creates the aryl nitrine which undergoes high efficiency C—H insertion into the xerogel superstructure. After being illuminated for 10 min, the Ovalbumin-templated xerogel films were rinsed with aqueous buffer (phosphate buffered saline, pH 7.0, 0.01 M, 15 mM NaCl) to liberate any Ovalbumin and unreacted 1 from the templated xerogel. The washing step also removed any Ovalbumin to which 1 may have reacted.

EXAMPLE 3

Figure 4:
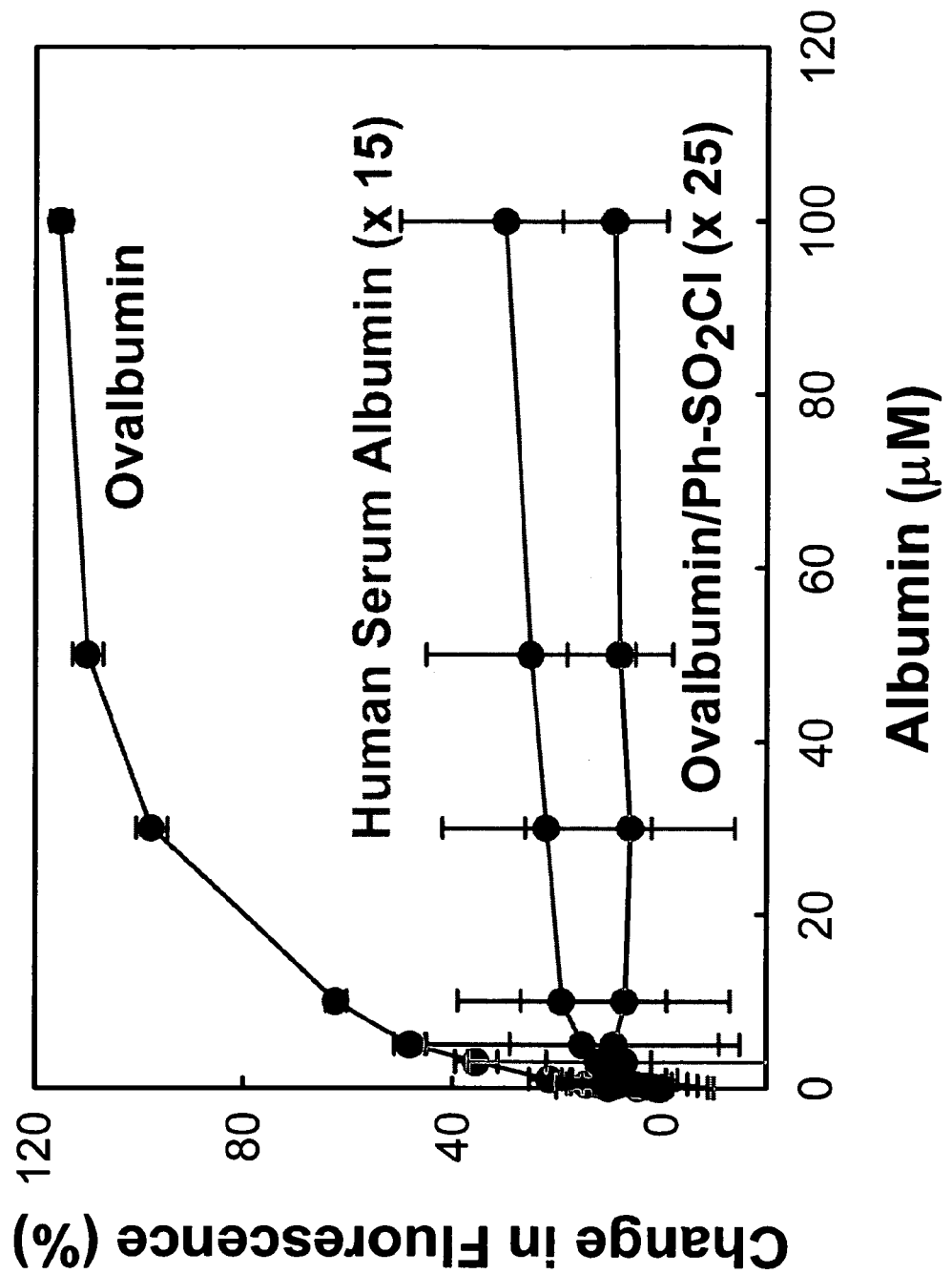
FIG. 4 is a representation of calibration curves for an Ovalbumin selective PIXIES.

This example describes the detection of ovalbumin by using the PIXIES prepared as described in Example 2. FIG. 4 summarizes the response profiles from a series (n=10) of Ovalbumin-templated PIXIES films. The molar composition of these particular PIXIES-based films was 55% tetraethylorthosilane (TEOS), 2% aminopropyltriethoxysilane (APTES), 3% octyltrimethoxysilane (OTS), and 40% bis (2-hydroxy-ethyl)aminopropyltriethoxysilane (HAPTS). The molar ratio of Ovalbumin:alkoxide Si was 1:750 and BODIPY 505/515 was used as the luminescent reporter molecule (RM in FIG. 2). As shown in FIG. 4, when Ovalbumin is added to these Ovalbumin-templated PIXIES the luminescence increases.

EXAMPLE 4

This example describes the selectivity of PIXIES for Ovalbumin. As an initial test of the Ovalbumin-templated PIXIES selectivity for Ovalbumin a solution of 15 micromolar Ovalbumin was reacted it with a 15-fold molar excess of phenyl-SO$_2$Cl to block all of the accessible primary amines on Ovalbumin surface. Then the response of PIXIES to the Ovalbumin sulfonamide was re-determined. There was no observable response (FIG. 4) over the concentration range tested (up to 2.5 mM).

In a second experiment we tested the Ovalbumin-templated PIXIES selectivity by using human serum albumin (HSA) as a surrogate interferent. The results of these experiments also showed (FIG. 4) that the Ovalbumin-templated PIXIES are selective for Ovalbumin over HSA (cf., Table 1 also).

In a third experiment we took a series of identical Ovalbumin-templated PIXIES and incubated them in mixtures of Ovalbumin, Ovalbumin sulfonamide, and HSA, we observed responses that were equivalent only to the Ovalbumin content of the samples.

In a fourth experiment we carried out a series of continuous flow experiments with an Ovalbumin-templated PIXIES sensor by injecting plugs of Ovalbumin followed by pure buffer. The response time (time to reach 90% of the maximum signal change) for these 625±10 nm thick PIXIES films was on the order of 45 s and the response is reversible to within 8% (25 cycles).

EXAMPLE 5

This example describes Scatchard analysis [20] on a series of PIXIES-based sensor films that were prepared by using different precursors and xerogel compositions. The results of these experiments are summarized in Table 1. The results of these experiments indicate that different xerogel compositions can be used to tune the PIXIES response and selectivity.

TABLE 1

Response and binding affinity from three ovalbumin (O)-templated PIXIES based on different precursor compositions.

| PIXIES Composition | O Response[b] | $K_d$ (nM)[a] | | |
|---|---|---|---|---|
| | | O | O Sulfonamide | HSA |
| A | 102 | 8/35 | — | 3000 |
| B | 167 | 2/19 | 79 | 352 |
| C | 65 | 18/125 | 56/289 | 650 |

[a]Where there are two entries this reflects the two recovered binding affinities.
[b]Reponse to 50 μM O (%).
[A] Same composition used for FIG. 4.
[B] 15% TEOS, 5% OTS, and 75% HAPTS.
[C] 8% TEOS 14% APTES, 7% OTS, and 71% HAPTS.

The equilibrium binding data presented in Table 1 demonstrates that substantial differences in response can be detected for one analyte over another and therefore tunable sensors can be designed for each analyte. This is further described further below.

EXAMPLE 6

Figure 5:
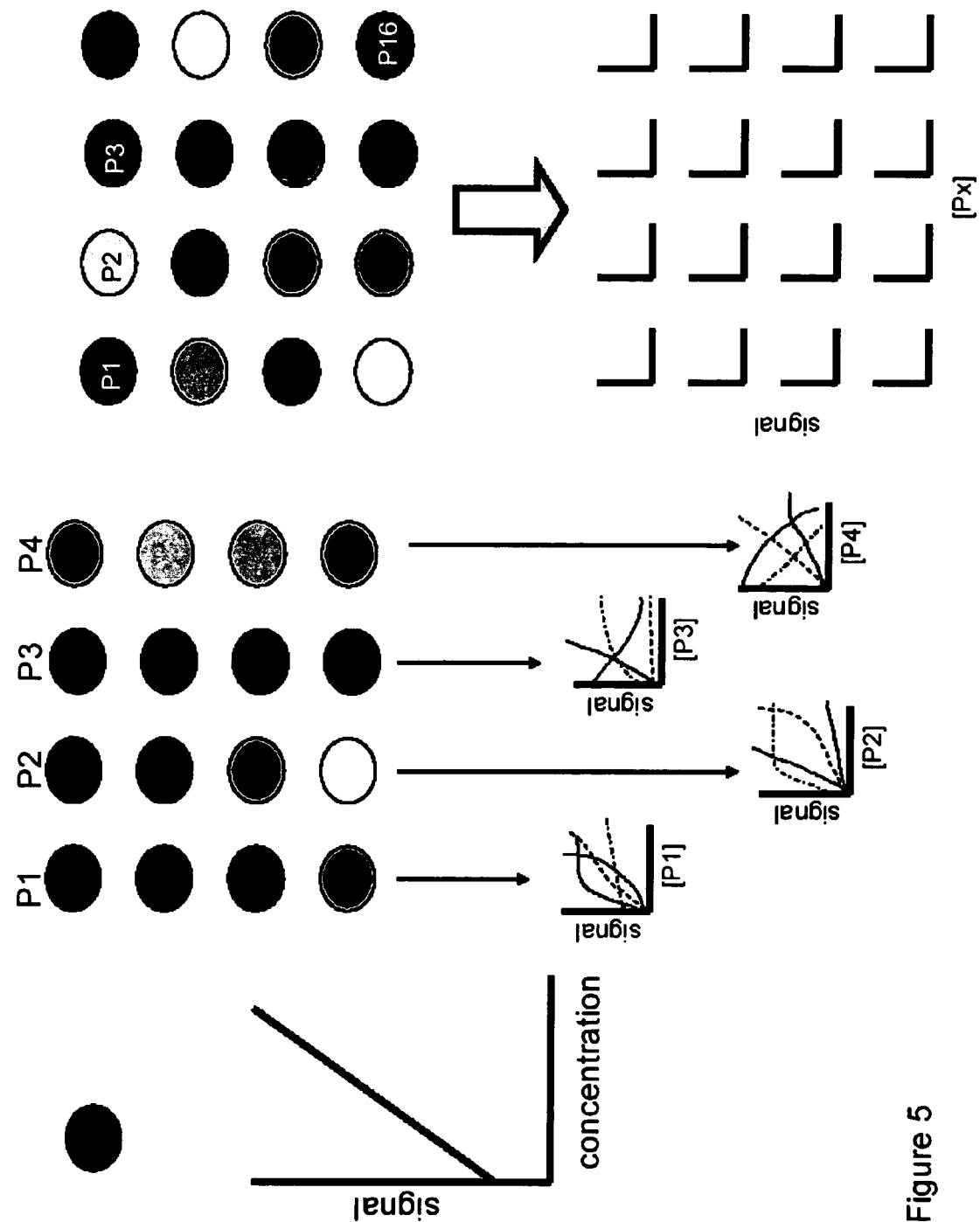
FIG. 5 is a representation of the progression from discrete sensor elements (left) to suites of redundant sensors (center) to a diversified multi-modal sensor array strategy (right).

This example (FIG. 5) describes the progression of PIPIES-based sensing platforms from discrete sensor elements (left) to suites of redundant sensors (center) to a diversified multi-modal sensor array strategy (right). Calibration curves are depicted below each array. The different circles represent different sensor elements based on different PRs, ADDs, ARs, Ts, and PTs (FIGS. 1-3). The strategy can be used to design and develop tailored PIPIES-based sensor platforms that can be used for improving selectivity for one protein over others or for simultaneous multi-protein detection and quantification in a single sample. This aspect of the invention is discussed in more detail below.

EXAMPLE 7

Figure 6:
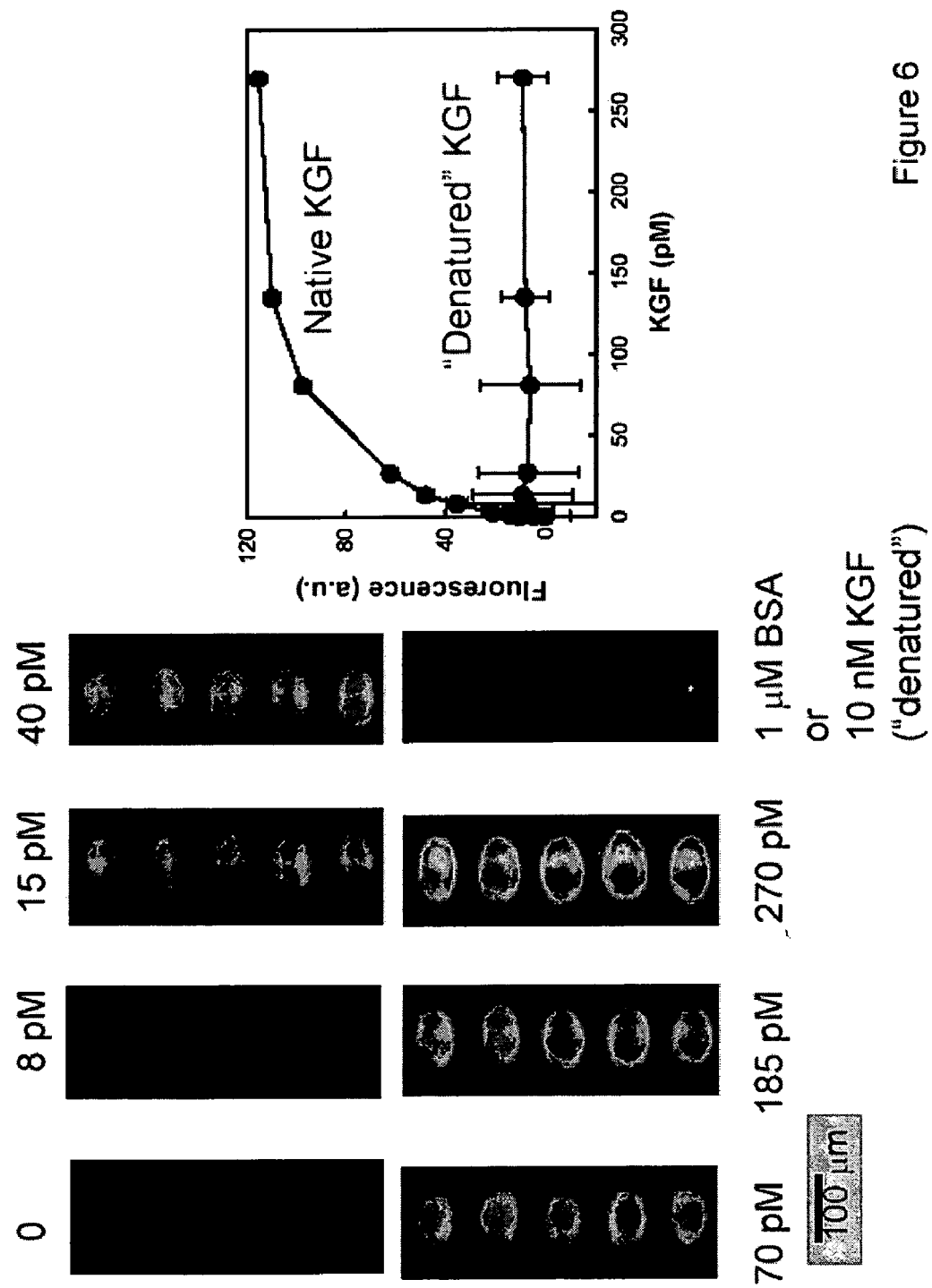
FIG. 6 is a representation of the response from five (5) replicate PIXIES-based sensor elements (100 micrometers in diameter) that have been designed for keratinocyte growth factor (KGF). Analytical calibration curves are also shown for these KGF-responsive PIXIES responding to native and denatured KGF.

In this example, the applicability of the PIXIES strategy in an array format is shown for the detection of keratinocyte growth factor (KGF). Here, five (5) identical PIXIES-based sensor elements were prepared in an array format for KGF. The results are summarized in FIG. 6. In the left hand portion of FIG. 6 is shown a series of CCD images of 100 micrometer diameter PIXIES-based sensors elements printed on the face of a LED and detected by a CCD as a function of added KGF. The emission from the PIXIES increases as the KGF concentration increases. A control experiment with a high concentration of BSA (1 micromolar) or chemically denatured KGF (i.e., KGF treated with 2 M urea) is also presented. The signal is equivalent to the blank. The right hand side of FIG. 6 presents the calibration curve for the KGF-templated PIXIES in the presence of native KGF and chemically denatured KGF. The selectivity is clear as is the detection potential of the PIXIES.

EXAMPLE 8

Figure 7:
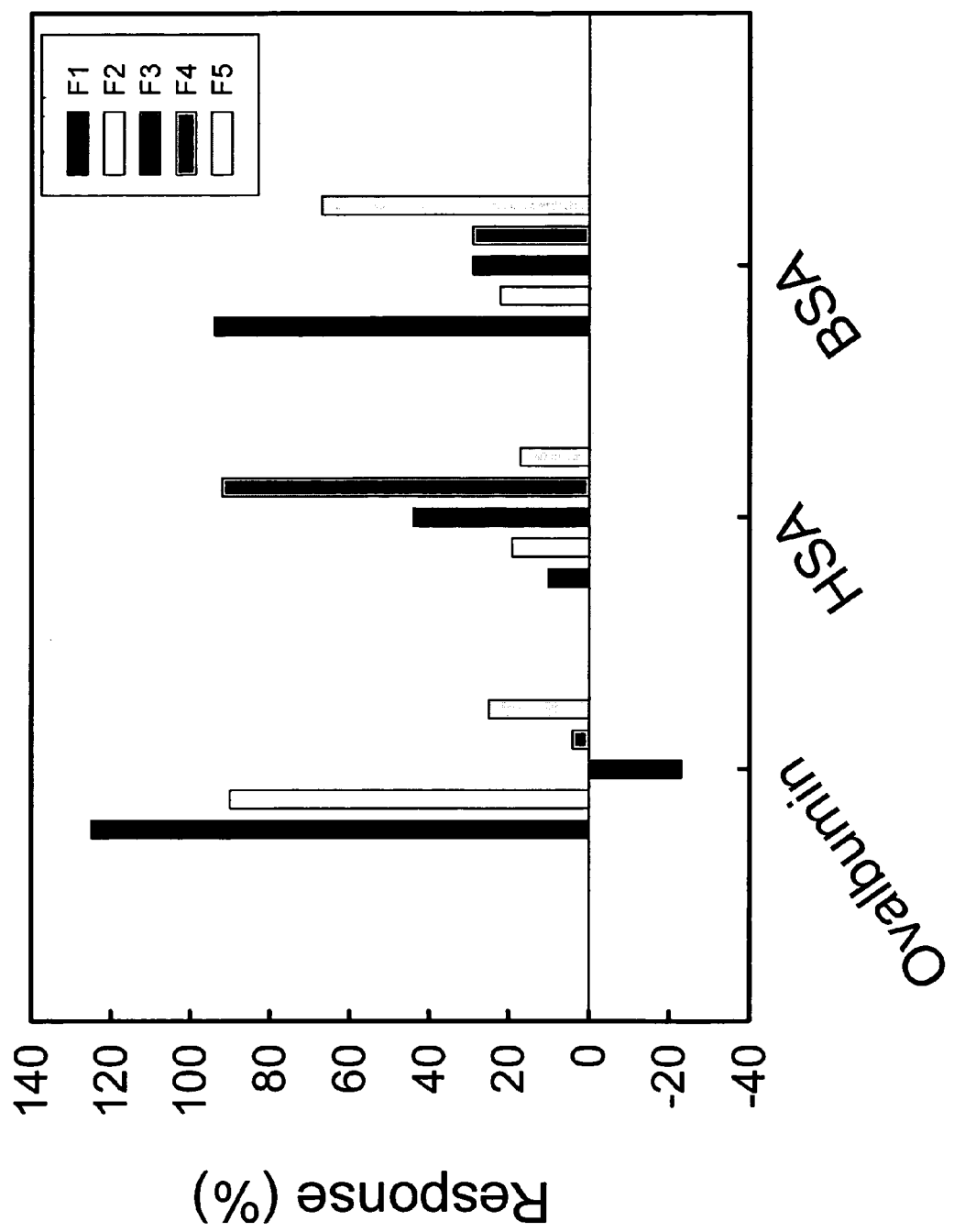
FIG. 7 is a representation of the response results (protein concentration=0.1 micromolar) from five (5) different PIXIES-based sensor elements derived from different xerogel precursor formulations (Fx) each templated for ovalbumin, human serum albumin (HSA), or bovine serum albumin (BSA).

In this example the response from a series of five (5) replicate PIXIES-based sensor elements, designed for Ovalbumin, HSA, and BSA, wherein each PIXIES is based on a different xerogel formulation. The results are shown in FIG. 7. Specifically, formulation F1 is 15% TEOS, 5% OTS, and 75% HAPTS; formulation F2 is 8% TEOS, 14% APTES, 7% OTS, and 71% HAPTS; formulation F3 is 8% TEOS, 14% APTES, 7% OTS, and 71% HAPTS doped with 3 weight % PEG (2000); formulation F4 is 28% TEOS 4% APTES, 7% OTS, and 61% HAPTS; and formulation F5 is 8% TEOS 14% APTES, 7% OTS, and 71% HAPTS with 1.5 mole % glycerol. By using such multiple sensors in concert, the overall detection accuracy, precision, and dynamic range for a given protein can be improved by several fold. False positives and negatives are also more readily detected by using multiple tunable sensors and redundant detection schema.

EXAMPLE 9

In this example, the applicability of this method to the detection of different proteins is demonstrated. A series of protein-templated xerogels were prepared and proteins were detected as in Examples 1 and 2.

The results are summarized in Table 2.

TABLE 2

Detection limits and selectivity factors for KGF-, interlukin-1α (IL-1α), interlukin-1β (IL-1β), transforming growth factor-α (TGF-α), and transforming growth factor-β (TGF-β)-templated PIXIES.

| Template | Detection Limits (pM) | Selectivity Factor[a] |
|---|---|---|
| IL-1α | 12 | 47[b] |
| IL-1β | 13 | 36[c] |
| KGF | 6 | 210[d] |
| TGF-α | 9 | 150[e] |
| TGF-β | 8 | 123[f] |

[a]Signal of the target protein at 5× the detection limits divided by the signal for an equivalent concentration of the interfering protein.
[b]IL-1β is the interfering protein.
[c]IL-1α is the interfering protein.
[d]Chemically denatured KGF (2 M urea) is the interfering protein.
[e]TGF-α is the interfering protein.
[f]TGF-β is the interfering protein.

These results show that the PIXIES strategy is capable of yielding discrete sensor elements that have low picomolar (pM) detection limits and that are selective for one protein over another protein when the proteins in question have high series homology. As an example, results in Table 2 are presented for PIXIES that were designed for interlukin-1α (IL-1α) and interlukin-1β (IL-1β) and transforming growth factor-α (TGF-α) and transforming growth factor-β (TGF-β). The selectivity factor for each sensor is at least 36-fold.

EXAMPLE 10

Figure 8:
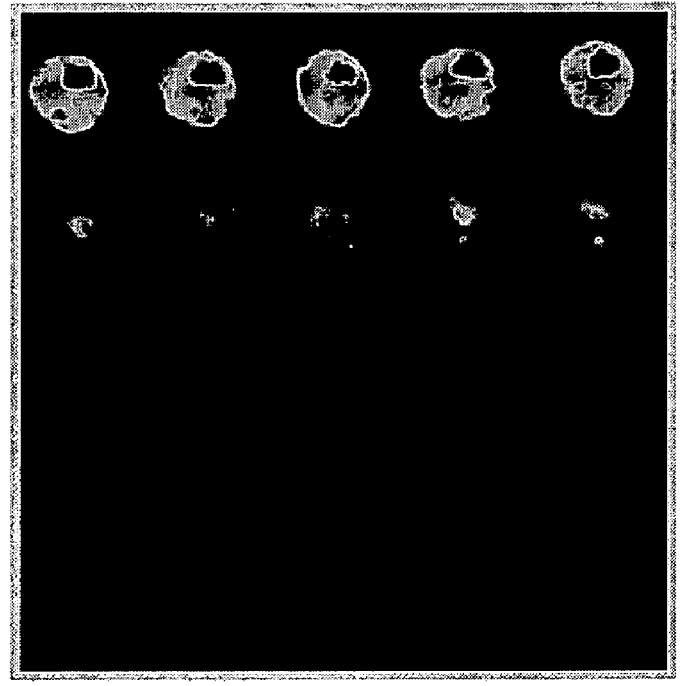
FIG. 8 is a representation of a portion of a diversified PIXIES-based sensor array that has been designed for intact Ricin (A and B chains). The response from five (5) replicates (columns) of five (5) different (rows) PIXIES-based sensor elements derived from different xerogel precursor formulations (Fx) is shown.
Figure 8:
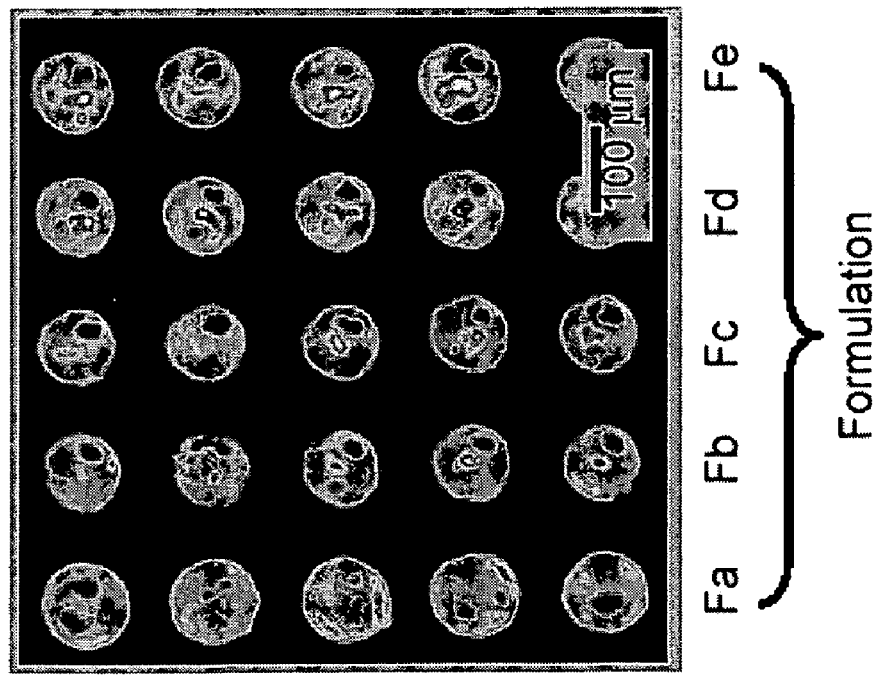

In this example, the development of a diversified PIXIES-based sensor array for the detection of Ricin is illustrated. Raw, false color CCD images from the epi-fluorescence microscope are shown for a 5×5 array of PIXIES-based sensor elements designed for intact Ricin (FIG. 8). Each column is composed of five (5) replicate sensor elements based on a given xerogel formulation chemistry (Fx). The AR in this cases is shown in FIG. 2 with RM=dansyl; the tether was a —(CH$_2$)$_3$—. Formulation Fa is 15% TMOS, 75% OTS, and 5% HAPTS; formulation Fb is 18% TEOS, 3% APTES, 8% OTS, and 71% HAPTS; formulation Fb is 8% TMOS 14%

APTES, 7% OTS, and 71% HAPTS doped with 12 weight % PEG (2000); formulation Fd is 25% TMOS, 7% APTES, 18% OTS, and 50% HAPTS; and formulation Fe is 20% TEOS, 10% APTES, 45% OTS, and 25% HAPTS with 3 mole % propylene glycol. By using such multiple sensors in concert, the overall detection accuracy, precision, and dynamic range for Ricin detection is improved by more than an order-of-magnitude and the dynamic range is extended significantly.

EXAMPLE 11

Figure 9:
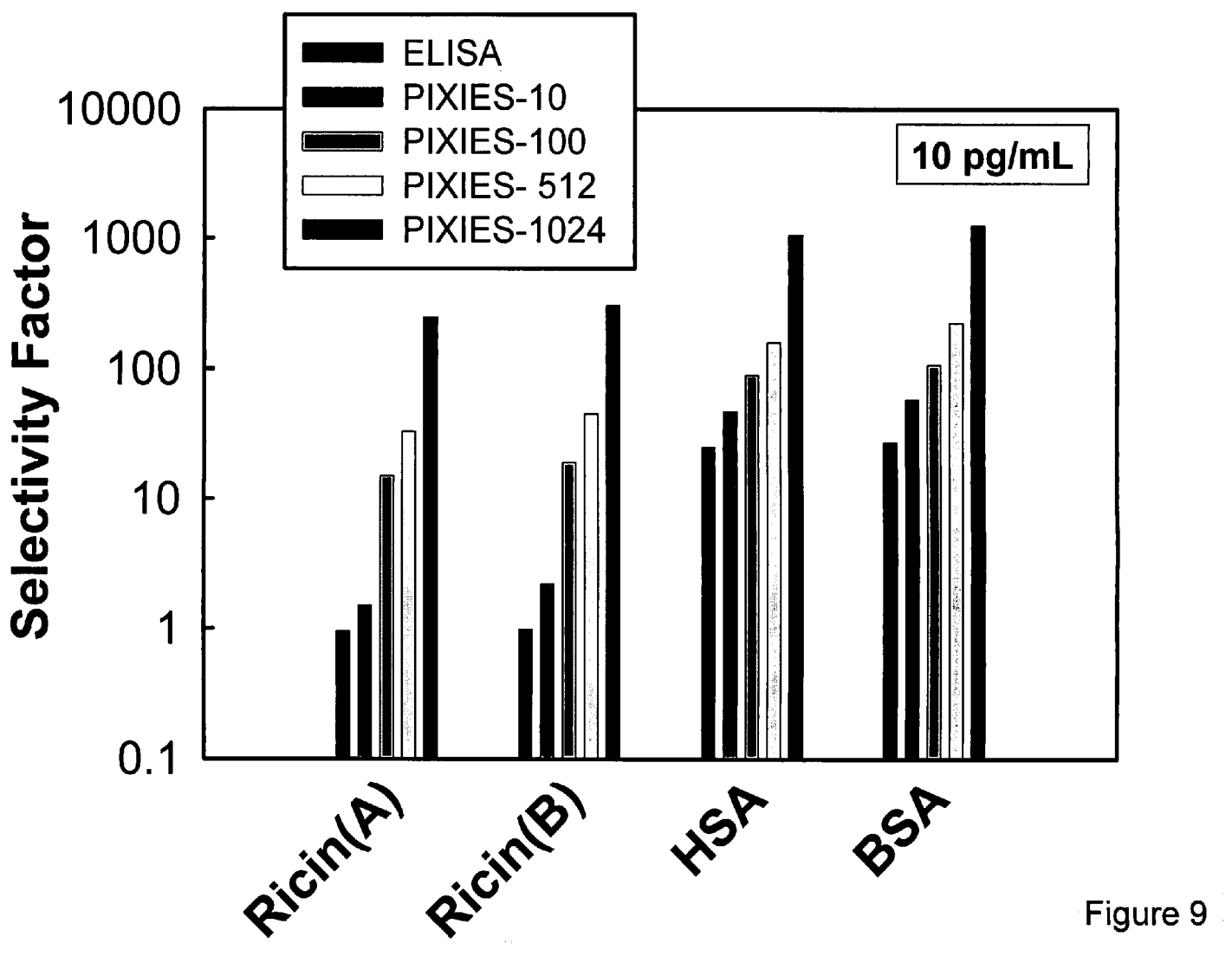

In this example, the selectivity of a standard enzyme linked immunoadsorption assay (ELISA) for intact Ricin is compared to the selectivity from four (4) diversified PIXIES-based sensor arrays that were composed of 10, 100, 512, and 1024 sensor elements each (FIG. 9). Each sensor element was derived from a different xerogel formulation (see FIG. 3 and Examples 3-10). The selectivity factor represents the collective response ratio from the ELISA or the indicated sensor array to 10 pg/mL of intact Ricin (A and B chain) divided by the collective response seen for the ELISA or same array when challenged with 10 pg/mL of the indicated protein (Ricin A only, Ricin B only, HSA, and BSA). The tremendous increase in selectivity seen for the PIXIES-based platform having many sensor elements in comparison to the ELISA is noticeable (over two orders of magnitude).

EXAMPLE 12

Figure 10:
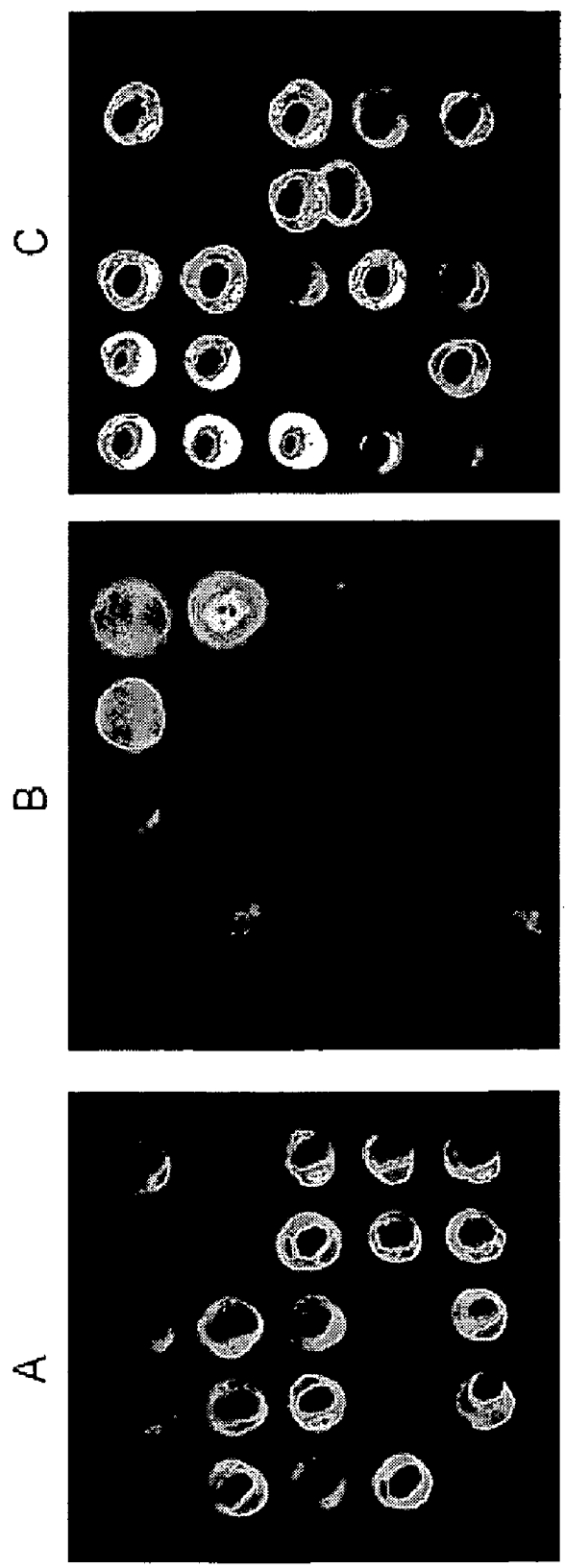
FIG. 10 is a representation of a portion of a 5×5 array of PIXIES-based sensor elements designed for the detection of 25 different proteins.

In this example, the applicability of the PIXIES strategy to the simultaneous, multi-modal detection of different proteins is demonstrated. Here, a 5×5 array of PIXIES-based sensor elements (FIG. 10) wherein each PIXIES-based sensor element is designed for a different protein target is challenged by three different protein mixtures. In FIG. 10A, the response from a mixture that contains HSA, BSA, Ovalbumin, KGF, IL-1, and TGF is shown. In FIG. 10B, the response from a mixture of KGF, calmodulin, porcine serum albumin, RANTES, and EGF is shown. In FIG. 10C the response from a mixture of HSA, RANTES, EGF, IL-1, and TGF is shown. These results demonstrate simultaneous, multi-protein detection in a sample.

While specific embodiments have been presented in this description, those skilled in the art will recognize that routine modifications can be made by those skilled in the art without departing from the scope of the invention.

REFERENCES

1. *Commercial Biosensors. Applications to Clinical, Bioprocess, and Environmental Samples*; Ramsay, G., Ed.; John Wiley & Sons: New York, N.Y., 1998.
2. Harris, T. D., *Anal. Chem.* 2000, 72, 669A.
3. Gopel, W., *Sens. Actuators B* 2000, B65, 70-72.
4. Albert, K. J.; Lewis, N. S.; Schauer, C L.; Sotzing, G. A.; Stitzel, S. E.; Vaid, T. P.; Walt, D. R., *Chem. Rev.* 2000, 100, 2595-626.
5. Britton, C. L.; Jones, R. L.; Oden, P. 1.; Hu, Z.; Warmack, R. J.; Smith, S. F.; Bryan, W. L.; Rochelle, J. M., *Ultramicroscopy* 2000, 82, 17-21.
6. Bailey, R. A.; Persaud, K. C. In *Polymer Sensors and Actuators*; Osada, Y.; DeRossi, D. F., Eds.: Springer-Verlag, Berlin, Germany, 2000; PP. 149-81.
7. Stefan, R.-I.; Van Staden, J. F.; Aboul-Enein, H. Y., *Crit. Rev. Anal. Chem.* 1999, 29, 133-53.
8. Walt, D. R., *Cur. Opin. Chem. Biol.* 2002, 6, 689-95.
9. (a) Barko, G.; Abonyi, J.; Ulavay, J., *Anal. Chim. Acta* 1999, 398, 219-26. (b) Wachter, E. A.; Thundat, T., *Rev. Sci. Instrum.* 1995, 66, 3662-7.
10. (a) Grate, J. W., *Chem. Rev.* 2000, 100, 2627-47. (b) Park, J.; Groves, W. A.; Zellers, E. T., *Anal. Chem.* 1999, 71, 3877-86. (c) Ricco, A. J.; Crooks, R. M.; Osbourn, G. C., *Acc. Chem. Res.* 1998, 31, 289-96.
11. *Methods in Enzymology*, Mosbach, K., Ed., Vol. 135 and 136, Academic Press: Orlando, Fla., 1987.
12. *Protein Immobilization: Fundamentals and Applications*, Taylor, R. F., Marcel Dekker, Inc.: New York, N.Y., 1991; Chapter 8.
13. Weetall, H. H. *Immobilized Enzymes, Antigens, Antibodies, and Peptides: Preparation and Characterization*, Marcel Dekker, Inc.: New York, N.Y., 1975; Chapters 6 and 8.
14. (a) Piletsky, S. A.; Alcock, S.; Turner, A. P. F., *TrBC* 2001, 19, 9-12. (b) Katz, A.; Davis, M. E., *Nature* 2000, 403, 286-9. (c) Dickert, F. L.; Hayden, O., "Molecular imprinting in chemical sensing," *TrAC* 1999, 18, 192-9. (d) Kriz, D.; Ramstrom, O.; Mosbach, K., *Anal. Chem.* 1997, 69, 345A-9A. (e) Ensing, K.; De Boer, T., *TrAC* 1999, 18, 138-45. (f) Wulff, G.," *Ang. Chem., Int. Ed. Engl.* 1995, 34, 1812-32. (g) Mayes, A. G.; Mosbach, K., *TrAC* 1997, 16, 321-32. (h) Mosbach, K., *TrBS* 1994, 19, 9-14. (i) Mallik, S.; Plunkett, S. D.; Dhal, P. K.; Johnson, R. D.; Pack, D.; Shuck, D.; Arnold, F. H., *New. J. Chem.* 1994, 18, 299-304.
15. (a) Burow, M.; Minoura, N., *Biochem. Biophys. Res. Comm.* 1996, 227,419-22. (b) Sellergren, B., *Angew. Chem. Int. Ed. Engl.* 2000, 39, 1031-7. (c) Mosbach, K., *Anal. Chim. Acta* 2001, 435, 3-8. (d) Piletsky, S. A.; Piletska, E. V.; Bossi, A.; Karim, K.; Lowe, Turner, A. P. F., *Biosen. & Bioelec.* 2001, 16, 701-7. (e) Bossi, A.; Piletsky, S. A.; Piletska, E. V.; Righetti, P. G.; Turner, A. P. F., *Anal. Chem.* 2001, 73, 5281-6.
16. Leung, M. K.-P; Chow, C.-F.; Lam, M. H.-W.," *J. Mater. Chem.* 2001, 11, 2985-91.
17. (a) Turkewitsch, P.; Wandelt, B.; Darling, G. D.; Powell, W. S., *Anal. Chem.* 1998, 70, 2025-30. (b) Jenkins, A L., Uy, O. M.; Murray, G. M., *Anal. Chem.* 1999, 71, 373-8. (c) Matsui, J.; Higashi, M.; Takeuchi, T., *J. Am. Chem. Soc.* 2000, 122, 5218-9. (d) Liao, Y.; Wang, W.; Wang, B., *Bioorg. Chem.* 1999, 27,463-76. (e) Graham, A. L.; Carison, C A.; Edmiston, P. L., *Anal. Chem.* 2002, 74, 458-67.
18. *Chemical Processing of Advanced Materials*; Hench, L. L.; West J. K., Eds.; Wiley: New York, N.Y., 1992.
19. Jin, W.; Brennan, J. D., *Anal Chim. Acta* 2002, 461, 1-36.
20. Lulka, M. F.; Iqbal, S. S.; Chambers, J. P.; Valdes, E. R.; Thompson, R. G.; Goode, M. T.; Valdes, J. J., *Mater. Sci. Engr.* 2000, C11, 101-5.

The invention claimed is:

1. A molecularly imprinted polymer for detecting the presence of an analyte selected from the group consisting of polypeptide, peptide and protein, comprising a xerogel or aerogel polymer matrix comprising:
   a plurality of templated sites with each of the plurality of templated sites being specific for the analyte and having one or more reporter molecules selectively attached at the templated site,
   wherein substantially all of the reporter molecules are present at the templated sites, and wherein upon binding of the specific polypeptide, peptide or protein to the templated site, a change in the absorbance and/or emission of the reporter is observed.

2. The molecularly imprinted polymer of claim 1, wherein the reporter is selected from the group consisting of a luminophore and a chromophore.

3. The molecularly imprinted polymer of claim 2, wherein the luminophore is selected from the group consisting of fluorescein; boron- dipyrromethene (BODIPY); rhodamine; tris(4,7-diphenyl-1,10 -phenanthroline)ruthenium(II) ([Ru (dpp)$_3$]$^{2+}$) and quantum dots.

4. The molecularly imprinted polymer of claim 2, wherein the chromophore is selected from the group consisting of 4-nitroaniline; 2,6-diphenyl-4-(2,4,6-triphenyl-1-pyridinio) phenolate; 2,6-dichloro-4-(2,4,6-triphenyl-1-pyridinio)phenolate; and N,N-diethyl-4-nitroaniline.

5. The molecularly imprinted polymer of claim 1, wherein the analyte is keratinocyte growth factor, ovalbumin, bovine serum albumin, or human serum albumin.

6. A method for detecting the presence of an analyte in a test sample comprising the steps of:
   a) contacting the test sample with the molecularly imprinted polymer of claim 1; and
   b) detecting a change in the absorbance or emission from the reporter molecule upon exposure to the test sample, wherein a change in the absorbance or emission from reporter molecule indicates the presence of the analyte in the test sample.

7. A method of preparing a molecularly imprinted polymer for selectively detecting an analyte selected from the group consisting of protein and polypeptide comprising the steps of:
   a) allowing polymerization of unpolymerized polymer components in the presence of analyte molecules to form a polymer matrix having templated sites, wherein each templated site has an analyte molecule bonded thereto;
   b) releasing the analyte molecules from the templated sites thereby forming templated sites which are specific for the analyte;
   c) separately preparing an analyte-[activable reporter] complex, wherein the activiable reporter is formed by covalently bonding an activable chemical residue to a reporter molecule;
   d) contacting the templated sites with the analyte-[activable reporter] complexes;
   e) activating the analyte-[activable reporter] complex to form analyte-[activated reporter] complex and thereby effect binding of the reporter portion of the analyte-[activated reporter] complex to the templated site; and
   f) releasing the analyte molecule from the analyte-[activated reporter] complex thereby providing a molecularly imprinted polymer having a templated site and a reporter molecule bound at or near the site, and wherein the templated site is specific for the analyte.

8. The method of claim 7, wherein the polymer is a xerogel or aerogel.

9. The method of claim 7, wherein the step of preparing an analyte-[activable reporter] complex comprises the steps of covalently bonding a reporter molecule to an activable chemical residue to form an activable reporter and allowing one or more activable reporters to bind to an analyte molecule to form an analyte-[activable reporter] complex, wherein the analyte-[activable reporter] complex has one or more reporter molecules.

10. The method of claim 9, wherein the reporter molecule is covalently bonded to the activable chemical residue via a chemical tether.

11. The method of claim 10, wherein the tether is selected from the group consisting of methylene chains, ether chains, polydimethylsiloxane chains, polystyrene chains, amino acid chains and organic or inorganic oligomers.

12. The method of claim 9, wherein the activable chemical residue is a photoactivable chemical residue.

13. The method of claim 12, wherein the photoactivable chemical residue is selected from the group consisting of aryl azide, fluorinated aryl azides and benzophenone derivatives.

14. The method of claim 9, wherein the activable chemical residue is selected from the group consisting of isothiocyanates, succinimidyl esters, carboxylic esters, tetrafluorophenyl esters, carbonyl azides, sulfonyl chlorides, arylating agents, aldehydes, iodoacetamides, maleimides, alkyl halides, arylating agents, disulfides, dichlorotriazines, N-methylisatoic anhydride, aminophenylboronic acids, isocyanates prepared from acyl azides, acyl nitriles, hydrazines, hydroxylamines amines, carbodiimides, esterification reagents, diazoalkanes, alkyl halides, and trifluoromethanesulfonates.

15. The method of claim 7, wherein the reporter is a luminophore or a chromophore.

16. The method of claim 15, wherein the luminophore is selected from the group consisting of fluorescein; boron-dipyrromethene (BODIPY); rhodamine; tris(4,7-diphenyl-1,10-phenanthroline)ruthenium(II) ([Ru(dpp)$_3$]$^{2+}$) and quantum dots.

17. The method of claim 15, wherein the chromophore is selected from the group consisting of 4-nitroaniline; 2,6-diphenyl-4-(2,4,6-triphenyl-1-pyridinio)phenolate; 2,6-dichloro-4-(2,4,6-triphenyl-1-pyridinio)phenolate; and N,N-diethyl-4-nitroaniline.

18. A molecularly imprinted polymer prepared by a process comprising the following steps:
   a) allowing polymerization of unpolymerized polymer components comprising polymerizable precursors in the presence of an analyte selected from the group consisting of polypeptide, peptide and protein molecules to form a polymer matrix having a plurality of templated sites, wherein each of the plurality of templated sites has an analyte molecule bonded thereto;
   b) releasing the analyte molecules from a templated site thereby forming a templated site which is specific for the analyte;
   c) preparing an analyte-[activable reporter] complex, wherein the activable reporter is formed by covalently bonding an activable chemical residue to a reporter molecule;
   d) contacting the templated site from b) with the analyte-[activable reporter] complex;
   e) activating the analyte-[activable reporter] complex to form analyte-[activated reporter] complex, and thereby effecting binding of reporter portion of the analyte-[activated reporter] complex to the templated site; and
   f) releasing the analyte molecule from the analyte-[activated reporter] complex to obtain a molecularly imprinted polymer.

19. The molecularly imprinted polymer of claim 18, wherein the polymer is xerogel or aerogel.

20. The molecularly imprinted polymer of claim 18, wherein the reporter is selected from the group consisting of a luminophore and a chromophore.

21. The molecularly imprinted polymer of claim 20, wherein the luminophore is selected from the group consisting of fluorescein; boron-dipyrromethene (BODIPY); rhodamine; tris(4,7-diphenyl-1,10-phenanthroline)ruthenium(II) ([Ru(dpp)$_3$]$^{2+}$) and quantum dots.

22. The molecularly imprinted polymer of claim 20, wherein the chromophore is selected from the group consisting of 4-nitroaniline; 2,6-diphenyl-4-(2,4,6-triphenyl-1-pyridinio)phenolate; 2,6-dichloro-4-(2,4,6-triphenyl-1-pyridinio)phenolate; and N,N-diethyl-4-nitroaniline.

23. The molecularly imprinted polymer of claim 18, wherein the analyte is specific for keratinocyte growth factor, ovalbumin, bovine serum albumin, or human serum albumin.

24. The molecularly imprinted polymer of claim 18, wherein the reporter molecule is covalently bonded to the activable chemical residue via a chemical tether.

25. The molecularly imprinted polymer of claim 24, wherein the tether is selected from the group consisting of methylene chains, ether chains, polydimethylsiloxane chains, polystyrene chains, amino acid chains, organic oligomers and inorganic oligomers.

26. The molecularly imprinted polymer of claim 18, wherein the activable chemical residue is a photoactivable chemical residue.

27. The molecularly imprinted polymer of claim 26, wherein the photoactivable chemical residue is selected from the group consisting of aryl azide, fluorinated aryl azides and benzophenone derivatives.

28. The molecularly imprinted polymer of claim 18, wherein the activable chemical residue is selected from the group consisting of isothiocyanates, succinimidyl esters, carboxylic esters, tetrafluorophenyl esters, carbonyl azides, sulfonyl chlorides, arylating agents, aldehydes, iodoacetamides, maleimides, alkyl halides, arylating agents, disulfides, dichlorotriazines, N-methylisatoic anhydride, aminophenylboronic acids, isocyanates prepared from acyl azides, acyl nitriles, hydrazines, hydroxylamines amines, carbodiimides, esterification reagents, diazoalkanes, alkyl halides and trifluoromethanesulfonates.

* * * * *